United States Patent
Grün et al.

(10) Patent No.: US 7,108,770 B2
(45) Date of Patent: *Sep. 19, 2006

(54) PROCESS FOR THE PURIFICATION OF TOLUENE DIISOCYANATE INCORPORATING A DIVIDING-WALL DISTILLATION COLUMN FOR THE FINAL PURIFICATION

(75) Inventors: Marcus Paul Grün, Düsseldorf (DE); Bill Brady, Jr., Düsseldorf (DE); Berthold Keggenhoff, Krefeld (DE); Kai Verkerk, Hilden (DE); Hans-Peter Schal, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 279 days.

This patent is subject to a terminal disclaimer.

(21) Appl. No.: 10/687,157

(22) Filed: Oct. 16, 2003

(65) Prior Publication Data

US 2004/0118672 A1    Jun. 24, 2004

(30) Foreign Application Priority Data

Oct. 22, 2002  (EP)  .................................. 02023662

(51) Int. Cl.
  *B01D 3/14*    (2006.01)
  *C07C 263/10*  (2006.01)
  *C07C 263/20*  (2006.01)
  *C07C 265/10*  (2006.01)

(52) U.S. Cl. .................. 203/29; 203/71; 203/100; 560/347; 560/352; 560/359

(58) Field of Classification Search ................ 203/29, 203/71, 100; 560/347, 352, 359; 196/111; 202/158

See application file for complete search history.

(56) References Cited

U.S. PATENT DOCUMENTS

| | | | | |
|---|---|---|---|---|
| 2,471,134 | A |  | 5/1949 | Wright ........................ 196/100 |
| 2,908,704 | A | * | 10/1959 | Skiles .......................... 560/347 |
| 3,287,387 | A | * | 11/1966 | Denton et al. .............. 560/347 |
| 3,321,283 | A | * | 5/1967 | Ewald ......................... 422/225 |
| 3,499,021 | A | * | 3/1970 | Kober et al. ................. 560/347 |
| 3,987,075 | A | * | 10/1976 | Schnabel ..................... 560/352 |
| 4,076,577 | A | * | 2/1978 | Hetzel et al. ............... 159/47.1 |
| 4,745,210 | A | * | 5/1988 | Mita et al. .................... 560/41 |
| 4,851,570 | A |  | 7/1989 | Zaby et al. .................. 560/347 |
| 5,449,818 | A |  | 9/1995 | Biskup et al. ............... 560/347 |
| 5,849,947 | A | * | 12/1998 | Biskup et al. ............... 560/347 |

OTHER PUBLICATIONS

The Polyurethane Handbook (Oertel, G. (Editor), Polyurethane Handbook, Munich, Germany, (month unavailable) 1985, pp. 62-73, Dr. K. Schauerte "Isocyanates".

(Continued)

*Primary Examiner*—Virginia Manoharan

(57) ABSTRACT

Toluene diisocyanate is recovered from a crude distillation feed containing less than 2% by weight of phosgene by (a) fractionating the crude distillation feed containing less than 2% by weight of phosgene to remove the solvent and optionally the reaction residues to produce a crude toluene diisocyanate feed containing less than 20% by weight of solvent and (b) separating the crude toluene diisocyanate feed containing less than 20% by weight of solvent in a divided-wall distillation column into four product fractions P1–P4. P1 is a vapor phase low-boiler and solvent-enriched gas stream, P2 is a low-boiler and solvent-enriched product, P3 is a high boiler-enriched bottoms product containing toluene diisocyanate and P4 is a toluene diisocyanate product stream lean in low-boilers, high-boilers and reaction residues.

10 Claims, 1 Drawing Sheet

OTHER PUBLICATIONS

Industrielle Aromatenchemie (Franck H.-G. and Stadelhofer J., Berlin Germany: Springer Verlag, (month unavailable) 1987, p. 253, "Herstellung und Verwendung von Toluel-Derivaten".

Chem System's PERP Report for TDI/MDI (Chem Systems, Process Evaluation Research Planning TDI/MDI 98/99S8, Tarrytown, NY, USA: Chem System, (month unavailable) 1999, pp. 27-32, Toluene Diisocyanate (TDI).

Industrial & Engineering Chemistry Research 37, month unavailable 1998, pp. 3444-3454 Rakesh Agrawal and Zbigniew T. Fidkowski, Are Thermally Coupled Distillation Columns Always Thermodynamically More Efficient for Ternary Distillations?.

* cited by examiner

PROCESS FOR THE PURIFICATION OF TOLUENE DIISOCYANATE INCORPORATING A DIVIDING-WALL DISTILLATION COLUMN FOR THE FINAL PURIFICATION

BACKGROUND OF THE INVENTION

The present invention relates to an improvement of a toluene diisocyanate (TDI) recovery and purification process which uses a dividing wall column for the final purification of the TDI product. The process of the present invention benefits from the ability to achieve a higher TDI purity.

The field of art to which this invention pertains is a process for the purification of toluene diisocyanate (TDI) mixtures. TDI mixtures are generally produced by reacting toluene with nitric acid to yield dinitrotoluene (DNT), hydrogenating the resultant dinitrotoluene (DNT) to yield toluene diamine (TDA) and reacting the toluene diamine (TDA) with phosgene to give toluene diisocyanate (TDI). Toluene diisocyanate (TDI) is a commercial by available material which is particularly useful in the preparation of polyurethanes, polyureas and polyisocyanurate polymers, especially foamed polymers.

DE-A1-3736988 teaches that organic mono- or polyisocyanates are continuously prepared by reacting the corresponding mono- or poly-amine dissolved in an inert organic solvent with phosgene also dissolved in an inert organic solvent at a temperature under 150° C. The amine and phosgene solutions are combined and allowed to pass through one or more reaction columns connected in series and having at least 10 chambers in total separated from each other by perforated plates, the holes of which preferably have a maximum diameter of 20 mm.

EP-A1-570799 teaches that production of aromatic diisocyanates is effected by reaction of diamines and phosgene. The phosgene and diamine are at or above the boiling temperature of the diamine and the reaction has an average contact time of 0.5–5 seconds. The mixture is continuously passed through a cylindrical reaction space at 200–600° C. to complete the reaction with avoidance of back mixing. The gas mixture is then cooled to condense the diisocyanates, with the temperature being maintained above the decomposition temperature of carbamic acid chlorides corresponding to the diamines used. Uncondensed diisocyanate is washed out of the gas mixture with an inert solvent, and the inert solvent is recovered by distillation.

The *Polyurethane* Handbook (Oertel, G. (Editor), Polyurethane Handbook, Munich, Germany: Hanser Publishers, 1985, pp 62–73) gives a description of a state of the art phosgenation and distillation process for the production of toluene diisocyanate. In the distillation process, the solvent is completely removed from the crude TDI mixture as the top product from a solvent column, with this solvent being returned to the phosgenation or to the excess phosgene recovery. The remaining crude isocyanate bottoms stream from the solvent column is sent to a pre-flasher where two products are achieved: an isocyanate-rich overhead product and a residue-enriched bottoms stream which is fed to the residue removal. In the residue removal, the volatiles are then removed from this residue-enriched stream and condensed. The condensed volatiles from residue removal together with the condensed overhead stream from the pre-evaporation are then combined and fed to an isocyanate column. In the isocyanate column, the product isocyanate is recovered as a top stream while a high-boiler enriched bottoms stream is returned to the pre-evaporation step. This process is limited by the fact that the complete solvent removal is performed in one solvent column. While it is known that TDI yields are negatively affected by higher temperatures, complete solvent removal necessitates operating under relatively low pressures to achieve sump temperatures low enough to prevent a loss of yield, thus necessitating a large column. Moreover, the long residence-time of isocyanate together with residue in heating zones can lead to a higher rate of residue formation. Finally, condensation of the overhead stream from the pre-evaporation before feeding to the isocyanate column is energy inefficient.

In *Industrielle Aromatenchemie* (Franck H.-G. and Stadelhofer J., Industrielle Aromatenchemie. Berlin, Germany: Springer Verlag, 1987, p 253), a second state-of-the-art process is described. In the described process, the crude TDI-solvent mixture is fed to a two-step pre-evaporation step resulting in a low-boiling overhead vapor product and solvent-free residue-enriched bottoms product which is fed to the residue removal. In the residue removal process, the volatiles are then removed from this residue-enriched stream and condensed. The overhead product from the pre-evaporation is fed to a solvent column. In the solvent column, the solvent is completely removed as the top product, with the solvent being returned to the phosgenation or to the excess phosgene recovery. The remaining crude isocyanate bottoms stream from the solvent column is fed along with the condensed volatiles from residue removal to an isocyanate column. In the isocyanate column, the product isocyanate is recovered as a top stream while a high-boiler (polymeric isocyanate and hydrolyzable chloride compounds (HCC), and other non-volatiles) enriched bottoms stream is returned to the pre-evaporation step. This process is also limited by the fact that the complete solvent removal must be performed in one solvent column. As in the process described in the *Polyurethane Handbook*, complete solvent removal necessitates operating under relatively low pressures to achieve sump temperatures low enough to prevent a loss of yield, resulting in a large solvent column. However, this process, in comparison with the former process achieves a reduced residence-time of isocyanate together with residue in heating zones possibly leading to a lower rate of residue formation. Moreover, because there is no needless condensation of a vapor feed to the isocyanate column, this process will be more energy efficient.

From Chem System's *PERP Reportfor TDI/MDI* (Chem Systems, Process *Evaluation* Research Planning TDI/MDI 98/99S8. Tarrytown, N.Y., USA: Chem Systems, 1999, pp 27–32) for TDI/MDI it can be learned, that the fractionation of a crude TDI distillation feed product can be completed in the following manner. Normally, the liquid product from the de-phosgenation stage is sent to a pre-evaporator which produces a residue-rich liquid-phase as a bottom product and a vapor-phase product containing mainly solvent and isocyanate as an overhead product. The bottom product from the pre-evaporation is sent to a process for the removal of volatile compounds from the reaction residues (residue removal). The volatile components removed in the residue removal stage as well as the vapor-phase product from the pre-evaporator are sent to a solvent column, where an initial separation of the isocyanate from solvent is completed as well as the removal of any remaining phosgene. The resulting products are a phosgene-enriched top product, a relatively pure solvent stream as an intermediate product and an isocyanate-enriched bottoms product. The phosgene stream is then returned to the de-phosgenation process or to the excess phosgene recovery process. The solvent product is then used in the phosgenation section as well as in the excess phosgene recovery. The bottoms isocyanate-rich product is then sent to a second solvent removal column where the remainder of the solvent is removed. The top solvent product from this step, when relatively pure, can be used in phosgenation or excess phosgene recovery or can be returned to the primary solvent removal step. The final solvent-free bottoms isocyanate product is sent to an isocyanate column, resulting in an isocyanate top product and a residue and hydrolyzable chloride compound (HCC) enriched-bottom stream which is returned to the pre-evaporation or to the residue-removal stages. This process like the process described in *Industrielle Aromatenchemie*, in comparison with the process described in the *Polyurethane Handbook* achieves a reduced residence-time of isocyanate together with residue in heating zones possibly leading to a lower rate of residue formation. Additionally, like the process described in *Industrielle Aromatenchemie*, because there is no needless condensation of a vapor feed to the isocyanate column, this process will be more energy efficient than the process disclosed in the Polyurethane Handbook. It holds the additional advantage, that the solvent removal is completed in two-steps. By taking advantage of the fact that the solvent has a lower boiling point than the isocyanate, the majority of the solvent can be removed under higher pressure, thereby reducing the necessary investment cost for the solvent removal. Additionally, the use of two solvent removal steps adds to the flexibility of operation. However, the presence of a third column adds more complexity to the process.

In fractionation, it is sometimes desirable to separate a multi-component feed stream into a number of streams containing various fractions of desirable components in the product streams. For the case of one feed stream and two product streams, the separation can be accomplished by distillate and bottoms product draw. Further separation can be accomplished by repeating the two-product stream process to either the distillate or the bottoms streams. However, the introduction of additional columns will require a corresponding number of reboilers and condensers. That requirement, in turn, requires additional operating costs as the condensing and the reboiling process is being repeated. Numerous references can be found in prior art documenting efforts to lower both capital and operating costs in the separation of several fractions from a multi-component feed stream The benchmark of the lowest energy consumption has been set by the old and well-known PETLYUK system (Agrawal, R and Fidkowski, Z, "Are Thermally Coupled Distillation Columns Always Thermodynamically More Efficient for Ternary Distillations?", *Industrial & Engineering Chemistry Research*, 1998, 37, pp 3444–3454). In this configuration, a pre-fractionation column separates the feed into two streams using a split vapor stream from the main column's stripping section and a split liquid stream from the main column's rectifying section. The resulting vapor and liquid streams exiting from the pre-fractionation column are richer in light and heavy components respectively. These two semi-processed streams are then fed back to the main column. This configuration provides an advantage allowing the main fractionation column to enhance the purity of the side stream draw. In turn, the main fractionation column also provides the stripping section and the rectifying section with better quality feeds. The combined effect is a very efficient use of vapor/liquid traffic to yield three product streams. U.S. Pat. No. 2,471,134 teaches an improvement of the Petyluk process with a proposal to combine the pre-fractionation and main columns into one fractionation unit by erecting a partition along the center part of a column. The column is equipped with one overhead condenser and one bottom reboiler.

The dividing-wall distillation column described in U.S. Pat. No. 2,471,134 is a vertical column fractionating tower, equipped with reboiler and condenser, which is divided into four distinct column sections by the use of a center partition in the intermediate part of the column. These sections are a common bottom (stripping) and top (rectifying) sections, and the pre-fractionation and main fractionation sections in the intermediate part of the column are separated by a dividing-wall. The multi-component mixture is fed to the pre-fractionation section, the overhead product is taken from the common rectifying section, a bottoms product is taken from the common stripping section, and the intermediate product stream is taken as a side-product from the main fractionation section. One significant advantage of the use of a dividing-wall distillation column is the fact that the sidedraw product can be obtained from the dividing wall distillation column with lower-concentration of low-boiling impurities than that of a side product which is obtained from a simple sidedraw product column.

This dividing-wall distillation column is effective in overcoming the hydraulic limitations in the PETLYUK system. At the same time, it reduces capital costs by having only one common shell. The dividing-wall distillation column disclosed in U.S. Pat. No. 2,471,134 has found applications in several processes.

SUMMARY OF THE INVENTION

In the present invention, the use of the dividing-wall distillation column for the final purification of the TDI product in the TDI distillation process allows for a surprising improvement in TDI purity by the reduction of the amount of low-boiling impurities. This improvement in TDI purity is achieved with reduced energy requirements and investment costs as compared to a standard sidedraw column to achieve the same product quality. Examples of the impurities removed by this process include solvents, solvent impurities, aromatic monoisocyanates, chlorinated aromatic monoisocyanates, etc.

BRIEF DESCRIPTION OF THE DRAWING

The FIGURE is a schematic of a divided wall distillation column which is useful in the process for the purification of mixtures of TDI of the present invention.

DETAILED DESCRIPTION OF THE INVENTION

Figure 1:
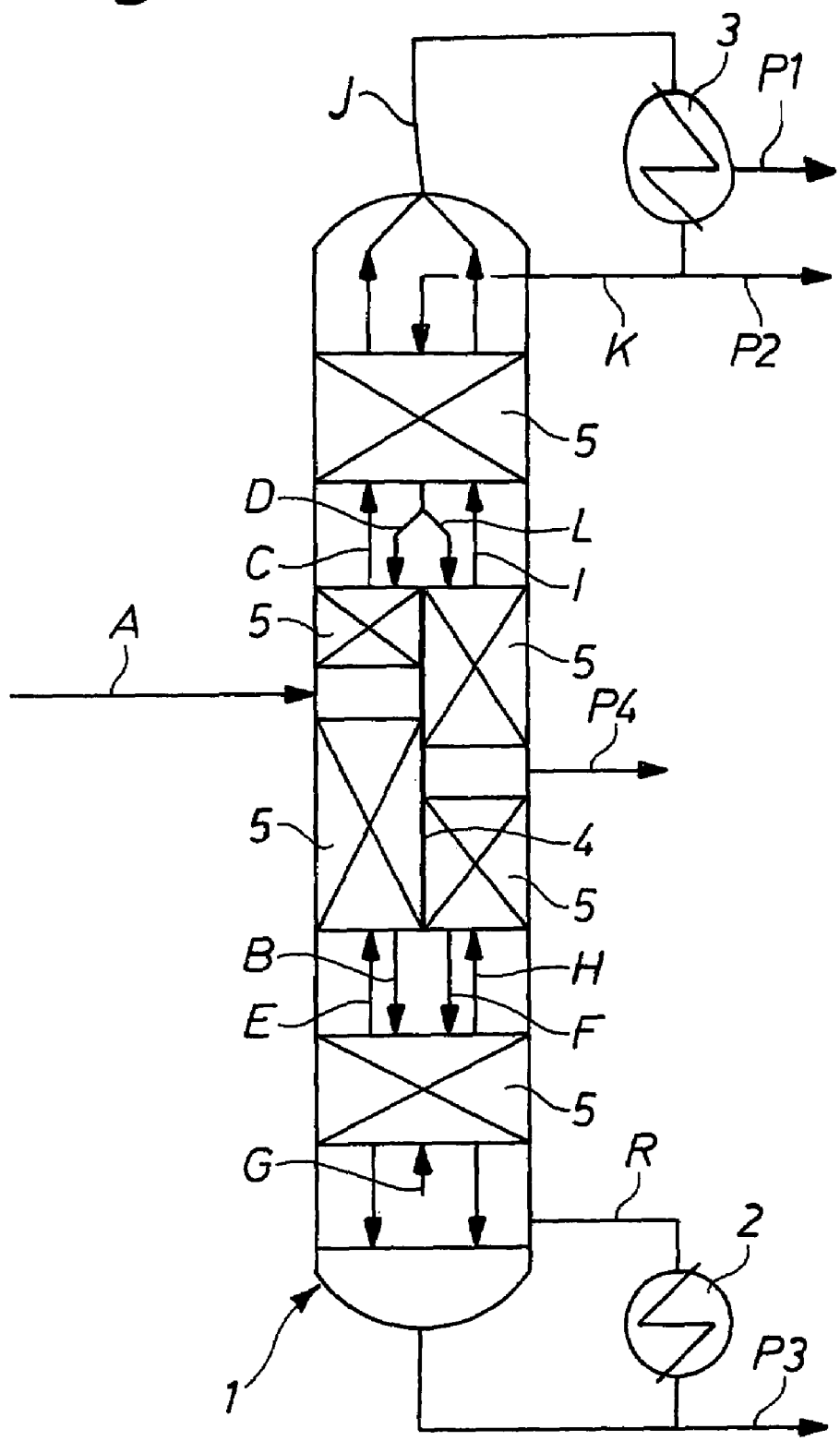

The present invention relates to a process in which toluene diamine is reacted with phosgene in the presence of a solvent in the liquid phase or to a process in which toluene diamine is reacted with phosgene directly in the gas phase with a solvent used in the quench cooling of said reaction. Excess phosgene is then partially or completely removed from the resulting reaction mixture and the de-phosgenated crude distillation feed is fed to a fractionation process in which the solvent and, optionally, the residue is (are) removed. The subsequent crude TDI feed is fed to a divided-wall distillation column in which four fractions are recovered:

1) a vapor phase low-boiler and solvent enriched product from which the condensable species are preferably recovered and returned to the de-phosgenation, residue removal, or solvent removal process;

2) a low-boiler enriched product which is then preferably returned to the de-phosgenation, residue removal, or solvent removal process or recovered as a separate product stream;

3) a high-boiler enriched bottoms product which is preferably sent to a residue removal system for the further recovery of volatiles; and 4) an isocyanate product stream.

A preferred embodiment of the invention is directed to a process for the purification of toluene diisocyanate from a crude distillation feed comprising less than 2% by weight of phosgene by a) fractionating the crude distillation feed comprising less than 2% by weight of phosgene to remove the solvent and, optionally, the reaction residues to produce a crude toluene diisocyanate feed comprising less than 20% by weight of solvent and b) separating the crude toluene diisocyanate feed comprising less than 20% by weight of solvent in a dividing-wall distillation column into four product fractions P1–P4, whereby P1 is a vapor phase low-boiler and solvent-enriched gas stream, P2 is a low-boiler and solvent-enriched product, P3 is a high boiler-enriched bottoms product comprising toluene diisocyanate and P4 is a toluene diisocyanate product stream which is lean in low-boilers, high-boilers and reaction residues.

The invention is also directed to a process for the production of toluene diisocyanate comprising the steps of a) reacting toluene diamine with phosgene to produce a crude distillation feed, b) separating the phosgene from the crude distillation feed from step a) if the crude distillation feed from step a) comprises 2% by weight or more of phosgene to obtain a crude distillation feed comprising less than 2% by weight of phosgene, c) fractionating the crude distillation feed comprising less than 2% by weight of phosgene to remove the solvent and, optionally, the reaction residues to produce a crude toluene diisocyanate feed comprising less than 20% by weight of solvent and d) separating the crude toluene diisocyanate feed comprising less than 20% by weight of solvent in a dividing-wall distillation column into four product fractions P1–P4, whereby P1 is a vapor phase low-boiler and solvent-enriched gas stream, P2 is a low-boiler and solvent-enriched product, P3 is a high boiler-enriched bottoms product comprising toluene diisocyanate and P4 is a toluene diisocyanate product stream which is lean in low-boilers, high-boilers and reaction residues.

The phosgenation is performed according to the state of the art. Toluene diamine is reacted with phosgene in the presence of a solvent solution in the liquid phase or with phosgene directly in the gas phase with a solvent used in the quench cooling of said reaction. The resulting reaction mixture preferably has a composition of 5–40% by weight toluene diisocyanate, 1–2% by weight hydrogen chloride, 1–5% by weight phosgene, 0.1-2% by weight high-boilers (polymeric isocyanates, hydrolyzable chloride compounds (HCC)), and the remainder solvent. In this case, hydrolyzable chloride compounds are defined as compounds in which the available chlorine is "loosely" bound. Illustrative of these compounds are the following species: $ClCH_2C_6H_3(NCO)_2$ and $(CH_3NCOCl)CH_3C_6H_3(NCO)$.

The content of hydrolyzable chloride compounds is generally determined by reacting the available chorine in the sample with a hot water-alcohol solution resulting in HCl and a subsequent titration to determine the hydrolyzable chloride concentration. This value is generally reported as weight fraction hydrolyzable chlorine" (HC).

Chlorinated aromatic hydrocarbons are species in which the chlorine is "tightly" bound. Illustrative of such chlorinated compounds are the common solvents o-dichlorobenzene, and chlorobenzene, and related compounds.

After the phosgenation reaction, the resulting reaction mixture is fed to a separation step if the reaction mixture (crude distillation feed) comprises 2% by weight or more of phosgene. In this separation step, the excess phosgene is at least partly removed to obtain a crude distillation feed comprising less than 2% by weight of phosgene. The separation of the phosgene can be performed using any of the many different known methods or combinations thereof. Examples of these known methods are simple vapor/liquid flash separation, with or without the increase of temperature or a decrease in pressure, gas stripping, distillation, etc.

The resulting crude distillation feed comprising less than 2% by weight of phosgene is then fed to a distillation column or system of distillation columns in which the solvent and, optionally, the reaction residue is (are) removed from the crude distillation feed comprising less than 2% by weight of phosgene to produce a crude toluene diisocyanate feed comprising less than 20% by weight of solvent. The distillation column(s) used for the removal of the solvent and optionally the reaction residues may be a conventional distillation column or a dividing wall distillation column. Preferably, a conventional distillation column according to the state of the art is used.

The resulting crude toluene diisocyanate feed comprising less than 20% by weight of solvent is then fed to a divided wall distillation column and separated into four product fractions P1–P4.

Product Fraction P1 is a vapor-phase low-boiler and solvent-enriched product comprising 20–99% by weight of condensible species ( i.e., solvent, low-boilers and TDI) with the rest being noncondensable gases (i.e., air, hydrogen chloride, etc.) The condensable fraction of this product may comprise solvent, low-boilers and TDI. The condensable species are preferably recovered and returned to the dephosgenation, residue removal, or solvent removal process.

Product Fraction P2 is a low-boiler and solvent-enriched product which is then preferably returned to the de-phosgenation, residue removal, or solvent removal process or recovered as a separate product stream. The product fraction P2 may comprise solvent, low boilers and TDI.

Product Fraction P3 is a high-boiler-enriched bottoms product which is preferably sent to a residue removal system for the further recovery of volatiles. The fraction P3 preferably comprises 0.5–15% by weight high-boilers (polymeric isocyanates, hydrolyzable chloride compounds (HCC), and other non-volatiles ), the remainder mainly toluene diisocyanate.

Product Fraction P4 is an isocyanate product stream. The fraction P4 preferably comprises less than 200 ppm by weight of solvent and / or chlorinated aromatic hydrocarbons (in total), less than 100 ppm by weight hydrolyzable chlorine (HC), less than 40 ppm by weight acidity, with a toluene diisocyanate concentration of at least 99.5% by weight.

The terms "low boiler" and "high boiler" are terms which are relative to the toluene diisocyanate being produced. That is, high boiler compounds are compounds having a boiling point that is greater than the boiling point of the TDI and low boiler compounds are compounds having a boiling point that is lower than the boiling point of the TDI.

The fractionation process including a divided-wall distillation column may be successfully utilized for the purification of a partially to fully de-phosgenated TDI reaction product resulting from the reaction of toluene diamine with phosgene in the presence of a solvent solution or from this reaction in the gas phase with a solvent used in the quench cooling after the reaction. The resulting distillation feed contains phosgene and other low-boiling components, solvent, toluene diisocyanate, hydrolyzable chloride compounds, and high-boiling residues. This stream is in turn fractionated to achieve the removal of the solvent and optionally the reaction residue to attain crude TDI which is then fed to a divided-wall TDI purification column. The four products from the divided-wall column are: (1) a low-boiler and inert gas-enriched product, from which the condensable species are preferably recovered and returned to the dephosgenation, residue removal, or solvent removal process; (2) a low-boiler enriched liquid product which is then preferably returned to the de-phosgenation, residue removal, or solvent removal process or recovered as a separate product stream; (3) a high-boiler-enriched bottoms product which is preferably sent to a residue removal system for the further recovery of volatiles; and (4) an isocyanate product stream. The solvent to be used can be any suitable solvent, preferably o-dichlorobenzene, p-dichloro-benzene, chlorobenzene, toluene, benzene, nitrobenzene, anisole, xylene, or any mixture thereof. Depending on reaction conditions, different concentrations of TDI in the crude distillation feed can be obtained.

The final purification of the crude toluene diisocyanate feed comprising less than 20% by weight of solvent is performed in a divided-wall distillation column such as that shown in the Figure. This divided-wall distillation column is equipped with at least one reboiler and one condenser. The reboiler can be any of the standard types commonly found in the chemical industry, including in part falling-film evaporators, forced circulation evaporators, pool boiling (kettle) evaporators, natural circulation evaporators, etc. The condenser can be any of the types in common use in the chemical industry including co-current and countercurrent (knockback condensers).The column can be equipped with any mass transfer internals that are in common use in the chemical industry. These include, in part, sieve trays, valve trays, fixed valve trays, as well as structured or random distillation packings.

The invention is described in more detail in the following with reference to the accompanying Figure.

The FIGURE shows a divided-wall distillation column 1 which is equipped with a reboiler 2, a condenser 3, a divided-wall 4 and mass transfer internals 5. The divided wall distillation column 1 is divided into four distinct operating zones, a pre-fractionation zone where the feed is introduced, a stripping zone with the high-boiler product P3, a main fractionation zone with the isocyanate product P4, and a rectifying zone with a vapor phase low-boiler product P1, and a liquid-phase low-boiler and solvent-enriched product P2. The pre-fractionation and the main fractionation zones lay side by side in the divided wall distillation column 1 with a dividing-wall 4 separating the two zones.

Pre-fractionation Zone

The crude distillation feed A is fed to the pre-fractionation zone in which that feed is separated into two streams, a residue and a hydrolyzable chloride compound (HCC)-enriched liquid TDI stream B and a low-boiler-enriched vapor stream C. This separation is effected by two streams, one liquid D and one vapor E. The liquid stream D, containing both low-boilers and TDI, enters the pre-fractionation zone from the rectifying zone. The vapor stream E, containing TDI and HCC's enters the pre-fractionation zone from the stripping zone.

Stripping Zone

The liquid product B from the pre-fractionation zone as well as the TDI and HCC-containing liquid product F from the main fractionation zone enter the upper section of the stripping zone. Vapor G generated from the reboiler 2 in stream R causes the separation of intermediate component from the heavy component. The resulting residue-enriched liquid containing high boiler is routed away as the bottoms product stream P3. The column is designed for an operating pressure so that the temperature achieved in the reboiler will preferably be in the range of from 140–190° C. The TDI-enriched vapor streams E and H are fed to the pre-fractionation zone and the main fractionation zone respectively. The distribution of the vapor flow to the pre-fractionation zone and main fractionation zone is effected by the inherent pressure drop in the respective column section.

Rectifying Zone

The low-boiler enriched vapor products C from the pre-fractionation zone and I from the main fractionation zone, both containing intermediate as well as low-boiling components enters the rectifying zone at the lower section. The vapor product J from the rectifying zone is fed to a condenser 3, and then a portion of the condensate product generated from the condenser is returned as reflux K to the top of the rectifying zone causing the separation of light component from the intermediate component. The remaining fraction of the condenser liquid product is routed away as the low-boiler and solvent-enriched liquid product stream P2. The uncondensed vapor product from the condenser is the low-boiler product stream P1. Internal reflux within the column generates a liquid stream. This liquid stream, containing mainly low-boilers and TDI, is divided into streams L and D which are routed to the main fractionation zone and to the pre-fractionation zone, respectively. The proportional distribution of these liquid streams is controlled to achieve the required product quality. Optionally, the product, P2 can be taken as a sidedraw product from any stage in the rectifying zone.

Main Fractionation Zone

A TDI-enriched vapor product stream H from the stripping zone enters the main fractionation zone from the bottom. A portion of the liquid product L from the rectifying zone enters the main fractionation zone from the top. The resulting fractionation generates three products: a vapor feed I to the rectifying zone, and a liquid feed F to the stripping zone, and a side draw product P4 that contains the desired quality isocyanate product. Optionally, the product P2 can be taken as a sidedraw product from any stage above the product removal stage for P4 in the main fractionation zone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the purification of toluene diisocyanate from a crude distillation feed comprising less than 2% by weight of phosgene comprising
   a) fractionating the crude distillation feed comprising less than 2% by weight of phosgene to remove solvent and, optionally, reaction residue to produce a crude toluene diisocyanate feed comprising less than 20% by weight of solvent and
   b) separating the crude toluene diisocyanate feed comprising less than 20% by weight of solvent in a divided-wall distillation column into four product fractions P1–P4 comprising: P1, a vapor phase low-boiler and solvent-enriched gas stream, P2, a low-boiler and solvent-enriched product, P3, a high-boiler-enriched bottoms product comprising toluene diisocyanate and P4, a toluene diisocyanate product stream lean in low-boiler, high-boiler and reaction residue.

2. The process of claim 1 in which the product fraction P1 comprises 20–99% by weight of the solvent, the low-boiler and toluene diisocyanate.

3. The process of claim 1 in which the product fraction P2 comprises the solvent the low boiler and toluene diisocyanate.

4. The process of claim 1 in which the product fraction P3 comprises toluene diisocyanate and 0.5–15% by weight of the high boiler.

5. The process of claim 1 in which the product fraction P4 has a toluene concentration of at least 99.5% by weight and comprises less than 200 ppm by weight of the solvent and/or chlorinated aromatic hydrocarbon, less than 100 ppm by weight hydrolyzable chlorine and less than 40 ppm by weight acid.

6. A process for the production of toluene diisocyanate comprising:
   a) reacting toluene diamine with phosgene to produce a crude distillation feed,
   b) separating any unreacted phosgene present in an amount greater than or equal to 2% by weight from the crude distillation feed to obtain a crude distillation feed comprising less than 2% by weight of phosgene,
   c) fractionating the crude distillation feed comprising less than 2% by weight of phosgene to remove solvent and optionally the reaction residue to produce a crude toluene diisocyanate feed comprising less than 20% by weight of the solvent and
   d) separating the crude toluene diisocyanate feed comprising less than 20% by weight of the solvent in a divided-wall distillation column into four product fractions P1–P4 comprising: P1, a vapor phase low-boiler and solvent-enriched gas stream, P2, a low-boiler and solvent-enriched product, P3, a high boiler enriched bottoms product comprising toluene diisocyanate and P4, a toluene diisocyanate product stream lean in low-boiler, high-boiler and reaction residue.

7. The process of claim 6 in which the product fraction P1 comprises 20–99% by weight of the solvent the low-boiler and toluene diisocyanate.

8. The process of claim 6 in which the product fraction P2 comprises the solvent, the low boiler and toluene diisocyanate.

9. The process of claim 6 in which the product fraction P3 comprises toluene diisocyanate and 0.5–15% by weight of the high-boiler.

10. The process of claim 6 in which the product fraction P4 has a toluene diisocyanate concentration of at least 99.5% by weight and comprises less than 200 ppm by weight of the solvent and/or chlorinated aromatic hydrocarbons, less than 100 ppm by weight hydrolyzable chlorine and less than 40 ppm by weight acid.

* * * * *